United States Patent [19]
Fujiwara et al.

[11] Patent Number: 5,951,535
[45] Date of Patent: Sep. 14, 1999

[54] ABSORPTIVE ARTICLE

[75] Inventors: Toshikatsu Fujiwara; Shingo Horiuchi, both of Moriyama, Japan

[73] Assignee: Chisso Corporation, Osaka-fu, Japan

[21] Appl. No.: 08/738,969

[22] Filed: Oct. 24, 1996

[30] Foreign Application Priority Data

Oct. 27, 1995 [JP] Japan .................................. 7-280532

[51] Int. Cl.$^6$ ................................................... A61F 13/54
[52] U.S. Cl. ........................................ 604/384; 604/367
[58] Field of Search ................................... 604/374, 378, 604/384, 367

[56] References Cited

U.S. PATENT DOCUMENTS

| | | | |
|---|---|---|---|
| 3,838,694 | 10/1974 | Mesek | 128/287 |
| 5,091,240 | 2/1992 | Kajander et al. | 428/198 |
| 5,600,974 | 2/1997 | Schnegg et al. | 66/192 |
| 5,700,254 | 12/1997 | McDowall et al. | 604/378 |

*Primary Examiner*—Robert A. Clarke
*Assistant Examiner*—Catherine Cogut
*Attorney, Agent, or Firm*—Fay, Sharpe, Beall, Fagan, Minnich & McKee

[57] ABSTRACT

An absorptive article containing a surface material comprising a combined non-woven fabric comprising at least two layers of a long fiber non-woven fabric and a short fiber non-woven fabric joined together and an absorbing body for retaining a body fluid is disclosed in which the short fiber non-woven fabric is composed of hot-melt-adhesive composite short fibers having at least two kinds of thermoplastic resin components of a high melting point component and low melting point component, and the hot-melt-adhesive composite short fibers are hot-melt-adhered together, the crossing angle of the short fibers at least preferably at least 45%, preferably at least 50% of the total contact points in the short fiber non-woven fabric are occupied by an angle of 60° to 90° in the analysis of the distribution of the crossing angle at the contact points of the fibers. An absorptive article is provided which is bulky and has a good hand feeling and touch, a good permeability of body fluids such as urine, blood, sweat, etc., a superior spot-absorption, a dryish feeling, and the property of a small back flow of the body fluids.

16 Claims, 1 Drawing Sheet

ABSORPTIVE ARTICLE

BACKGROUND OF THE INVENTION

1. Field of the Invention

This invention relates to an absorptive article comprising a combined non-woven fabric which is bulky, and has a good hand feeling and touch, and is used as a surface material. More particularly, the present invention relates to an absorptive article which is superior in the permeation-absorption and spot-absorption of a body fluid and in dryish feeling, and in the property of small back flow of the permeated body fluid all of which are required of absorptive articles such as disposable diapers and sanitary napkins.

2. Description of the Related Art

Various embodiments of absorptive articles formed so as to absorb body fluids such as urine, sweat, and blood nave been well known. In general, absorptive articles are composed of a liquid permeable (pervious) top sheet, a liquid impermeable back sheet and an absorptive body arranged between the top sheet and the back sheet. A single or a plural number of additional layers are sometimes additionally interposed between the above layers. Such additional layers may rapidly transport the body fluid. As the surface materials for the top sheet or back sheet, knit or woven fabrics, non-woven fabrics, films or composite materials thereof are used, and the required performances are varied. Since the surface materials touch human skins, bulkiness, excellent hand feeling, and good touch have been required. Further, for the top sheet, a high permeation-absorption and spot-absorption of a body fluid, a dryish feeling, and the property of a small back flow of the permeated body fluid have been required.

Since long fiber non-woven fabrics obtained according to a technique represented by a spun bonding process have a higher tenacity and are relatively cheap as compared with short fiber non-woven fabrics, the former have been used for various applications. However, the long fiber non-woven fabrics are inferior in the hand feeling as compared with short fiber non-woven fabrics, and in particular, when the former are used for the surface material of absorptive articles, it shows a drawback that they are inferior in the feeling such as the feeling when touched to skin. The reason that the feeling of the long fiber non-woven fabrics is inferior lies in that no crimp is developed in the long fibers from which the fabrics are formed, the apparent density is high, and thus the air content in the fabric is low. Accordingly, it can be considered that if crimps are developed in the long fibers, a long fiber non-woven fabric having a superior feeling can be obtained. However, it has been found that long fibers having crimps are difficult to effect uniform spreading, and in the case of long fibers having latent crimps, shrinkage occurs in the lengthwise direction of the long fibers when crimps are developed, whereby homogeneous long fiber non-woven fabrics can sometimes not be obtained.

On the other hand, short fiber non-woven fabrics obtained according to technique represented by a carding process are excellent in homogeneity and composed of crimped short fibers. Accordingly, they are bulky and have a good feeling such as to touch. However, since the short fiber non-woven fabrics are composed of an assembly of short fibers, they have a low strength as compared with long fiber non-woven fabrics, and have a drawback of readily being broken when they are used as a surface material of absorptive articles.

As described above, both long fiber non-woven fabrics and short fiber non-woven fabrics have merits and demerits. Thus, it has been difficult to make the merits coexistent in a single fiber layer. As the technique for making the merits of long fiber non-woven fabrics and short fiber non-woven fabrics coexistent, lamination of a long fiber non-woven fabric and a short fiber non-woven fabric is generally performed. Such a technique, for example, Laid-open Japanese Patent Publication No. Hei 6-136654 discloses a laminated or combined non-woven fabric obtained by laminating a long fiber non-woven fabric and a short fiber non-woven fabric, followed by subjecting the resulting laminate to a high pressure water steam treatment. However, since not only the short fiber non-woven fabric disclosed in the above technique, but also most of short fiber non-woven fabrics are obtained according to a carding process, short fibers which form the non-woven fabric are arranged in the lengthwise direction, i.e. mechanical direction of the non-woven fabric, whereby they are very anisotropic and inferior in the isotropy. Accordingly, when such non-woven fabrics are used as a surface material of absorptive articles, a capillary-like function is exercised in the short fiber non-woven fabrics and the laminated non-woven fabrics in the mechanical direction of the non-woven fabrics, and thus the body fluid is easily spread in the arranged direction of fibers at the time of absorption of the body fluid. Accordingly, the non-woven fabrics have drawbacks that they are not only inferior in the permeation-absorption, but also they easily retain the fluid. Even when they are subjected to a high pressure water stream treatment, the arrangement of the short fibers, after all, depend on the processing process of fibers into a non-woven fabric, i.e. a carding process. Thus, the short fiber non-woven fabrics and their laminated non-woven fabrics are as yet liable to retain the fluid, and the permeation-absorption and the spot-absorption of the body fluids is poor. Further, since the laminated non-woven fabric according to this technique has been subjected to a high-pressure water stream treatment, it has a high apparent density and is liable to cause the back-flow. Accordingly, when such a laminated non-woven fabric is used as a surface material of absorptive articles such as disposable diapers, sanitary napkins, particularly as top sheets, good permeation-absorption and spot-absorption of body fluid such as urine, sweat, and blood, dryish feeling and a small back flow of permeated body fluid which are inherently required of absorptive articles is unsatisfactory.

SUMMARY OF THE INVENTION

The present invention is to provide an absorptive article, comprising, as its surface material, a combined non-woven fabric having a high bulkiness and a good hand feeling and touch. Another object of the present invention is to provide an absorptive article having a superior permeation-absorption and spot-absorption of body fluids such as urine, sweat, and blood, and a small back flow property.

As a result of extensive research by the present inventors in order to solve the problems mentioned above, it has been found that when a non-woven fabric obtained by combining a long fiber non-woven fabric and a specific short fiber non-woven fabric is used as a surface material, an absorptive article having a high surface-strength, a good touch, a superior permeation-absorption and spot-absorption of body fluids can be provided, leading to the achievement of the present invention.

The present invention has the following aspects:

(1) An absorptive article containing a surface material comprising a combined non-woven fabric comprising at least two layers of a long fiber non-woven fabric and a short fiber non-woven fabric joined together, and an absorbing body for retaining a body fluid. The short fiber non-woven fabric is composed of hot-melt-adhesive composite short fibers having at least two kinds of thermoplastic resin components of a high melting point component and a low melting point component, and the hot-melt-adhesive composite short fibers are hot-melt-adhered together. The crossing angle of the short fibers at at least 45% of the total contact points in the short fiber non-woven fabric are occupied by an angle of 60° to 90° in the analysis of the distribution of the crossing angle at the contact points of the short fibers.

(2) An absorptive article according to aspect 1 wherein a body fluid-diffusing layer is interposed between the surface material and the absorbing body.

(3) An absorptive article according to aspect 1 wherein the long fiber non-woven fabric is composed of hot-melt-adhesive composite long fibers having at least two kinds of thermoplastic resin components of a high melting point component and a low melting point component, and the contact points between the hot-melt-adhesive composite long fibers are hot-melt-adhered.

(4) An absorptive article according to aspect 1 wherein the short fiber non-woven fabric is composed of fibers having a fiber length of 3 to 51 mm.

(5) An absorptive article according to aspect 1 or 4 wherein the short fiber non-woven fabric is composed of (A) hot-melt-adhesive composite short fibers having at least two kinds of thermoplastic resin components of a high melting point component and a low melting point component, and (B) hydrophilic short fibers, and the fiber-mixing ratio of A/B is 30/70 to 100/0.

(6) An absorptive article according to aspect 1, 4, or 5 wherein the short fiber non-woven fabric has a density gradient in the thickness direction of the non-woven fabric.

(7) An absorptive article according to aspect 2 wherein the body fluid-diffusing layer is an aggregate of crimped fibers.

(8) An absorptive article according to aspect 2 or 7 wherein the body fluid-diffusing layer is an aggregate of fibers comprising mixed long fibers or mixed short fibers.

(9) An absorptive article according to aspect 2 or 8, wherein the body fluid-diffusing layer is an aggregate of fibers having a not-circular cross-section.

(10) An absorptive article according to aspect 2 or 9, wherein the body fluid-diffusing layer is an aggregate of fibers containing a hydrophilic component.

BRIEF DESCRIPTION OF THE DRAWING

FIGS. 1 and 2 are typical views showing the main parts of an absorptive article of the present invention in which FIG. 1 shows an upper surface view and FIG. 2 shows a cross-sectional view along X–X' line in FIG. 1.

In FIGS. 1 and 2, 1 is an absorptive article (sanitary napkin), 2 is a top sheet, 3 is a back sheet, 4 is an absorbing body, 5 is a circular arc part of the absorptive article, 6 is a circular arc part of the absorbing body, 7 is a side part in lengthwise direction of the absorptive article, 8 is a wrapping material, 9 is a side part in lengthwise direction of the absorbing body, 10 is a body fluid-diffusing layer, 11 is an adhered layer, and 12 is a release liner.

DETAILED DESCRIPTION OF PREFERRED EMBODIMENTS

The present invention will be described in detail below.

The surface material referred to in the present specification includes not only a member which forms the surface of absorptive articles such as a top sheet, back sheet, and side gather, but also a member such as a wrapping material of the absorptive body and second sheet. Absorptive articles of the present invention are those which use a combined non-woven fabric at least as a top sheet or a second sheet among the surface materials. The combined non-woven fabric used as the surface materials are a non-woven fabric having a long fiber non-woven fabric and a short fiber non-woven fabric joined together. The short fiber non-woven fabric is composed of hot-melt-adhesive composite short fibers having at least two kinds of thermoplastic resin components of a high melting point component and a low melting point component, and the hot-melt-adhesive composite short fibers are hot-melt-adhered together. Further, the crossing angle of the short fibers at at least 45% of the total contact points in the short fiber non-woven fabric is occupied by an angle of 60° to 90° in the analysis of the distribution of the crossing angle at the contact points of the short fibers. Namely, the randomness of the short fibers which constitute the combined non-woven fabric is high, and further, the fibers are arranged comparatively in the thickness direction of the short fiber non-woven fabric. Thus, the combined non-woven fabric is characterized in that it is bulky and sufficiently reduced in the apparent density; the capillary-like function in the lengthwise direction, i.e. mechanical direction, of the non-woven fabric hardly occurs; hence the liquid is hardly retained; whereas the composite non-woven fabric is superior in the capillary-like function in the thickness direction. While the absorptive articles of the present invention comprise the combined non-woven fabric as the surface material, particularly as the top sheet or the second sheet, the articles exhibit advantageous effect such as good touch, a superior permeation-absorption and spot-absorption of the body fluids, and a small back flow of the body fluids.

Hereinafter, the absorptive articles of the present invention will be described in detail with reference to FIG. 1 and FIG. 2.

Figure 1:
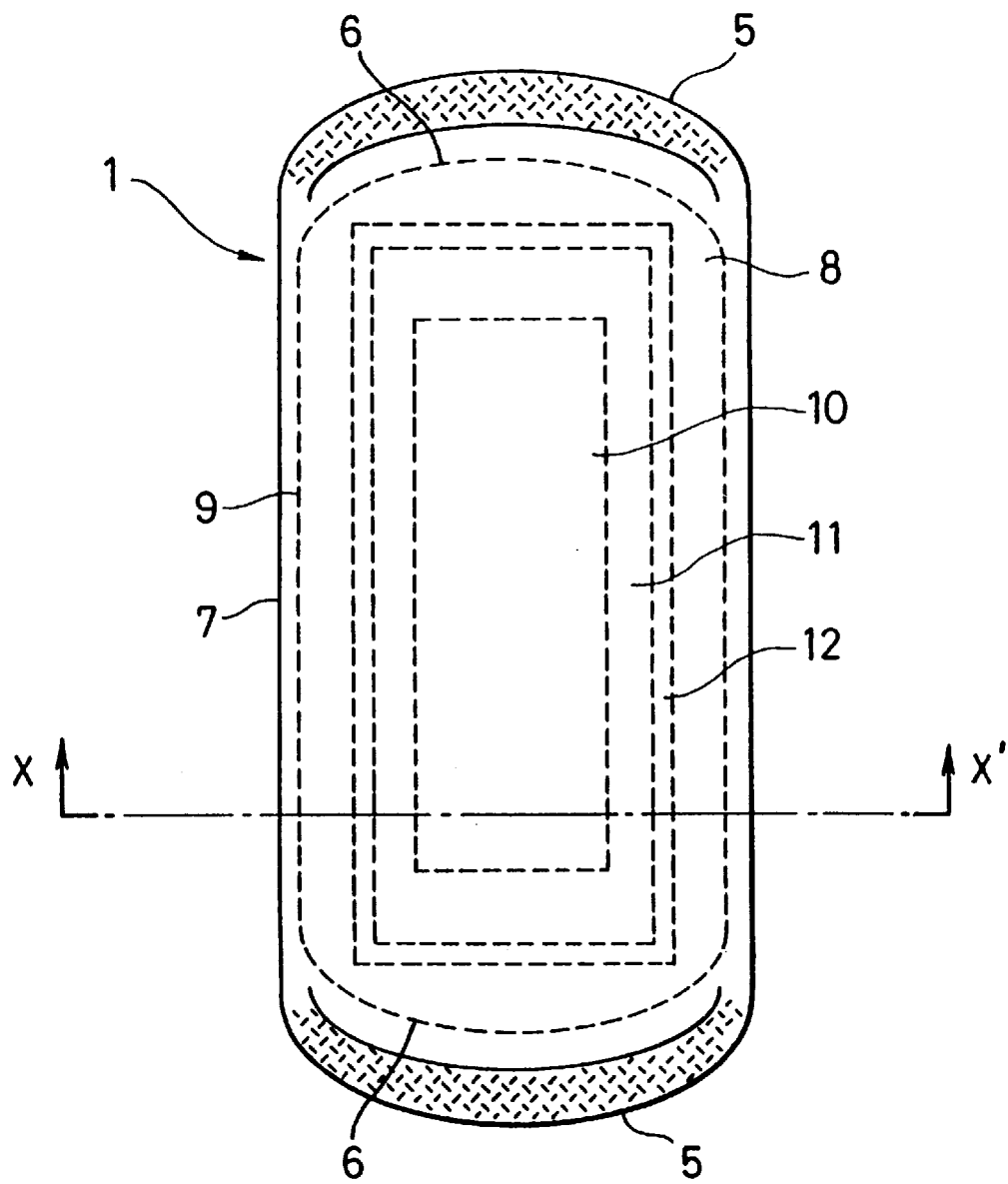

FIG. 1 shows the upper surface view of a sanitary napkin as an embodiment of the absorptive articles of the present invention. FIG. 2 shows a cross-sectional view along X–X' line in FIG. 1. The absorptive article of the present invention (sanitary napkin) 1 has a similar construction to that of the prior art in the aspect that the article is provided with a liquid-permeable top sheet 2, a liquid-impermeable back sheet 3, and an absorbing body 4 which is arranged therebetween to absorb and retain the body fluid.

Absorbing body 4 is wrapped with a wrapping material 8, and a body fluid-diffusing layer 10 is arranged between the wrapping material 8 and the absorbing body 4. Further, an adhesive layer 11 is provided on a back sheet 3 on the side which contacts with a panty, and a release liner 12 is arranged so as to cover the adhesive layer 11. While the sanitary napkin 1 may be formed into various shapes, in most cases, it has a rectangular shape, and its end margin parts are respectively formed in a shape of a circular arc 5. While the absorbing body 4 is generally smaller than the back sheet 3 and may be formed into various shapes, in most cases, it has a rectangular shape, and may be formed in a shape of a circular arc 6, corresponding to the shape of the back sheet 3. Side part 9 in lengthwise direction of the absorbing body 4 as an absorbing member and side part 7 in lengthwise direction of the absorptive article 1 may be curved toward the inside or may be narrowed to a certain extent at the central part, taking the fitting property at the time of use into consideration.

At least the top sheet 2, among the surface materials of the absorptive article having the construction mentioned above, is a combined non-woven fabric having a long fiber non-woven fabric and a short fiber non-woven fabric joined together. The short fiber non-woven fabric is composed of hot-melt-adhesive composite short fibers having at least two kinds of thermoplastic components of a high melting point component and a low melting point component, and the hot-melt-adhesive composite short fibers are hot-melt-adhered to each other. The crossing angle of the short fibers at 45% or more of the total contact points in the short fiber non-woven fabric is occupied by an angle of 60° to 90° in the analysis of the distribution of the crossing angle at the contact points of the short fibers.

Composite non-woven fabric is obtained by laminating a long fiber non-woven fabric and a short fiber non-woven fabric and integrating them. The long fiber non-woven fabric is obtained by accumulating and joining long fibers together. Specifically, it can be obtained, for example, according to conventional processes such as a tow-spreading process and a spun-bonding process. As the long fibers which constitute the long fiber non-woven fabric, those having a denier of 0.5 to 6 d/f are usable. When the denier of the long fibers is less than 0.5 d/f, reduction in the spinnability due to high speed spinning for maintaining the productivity, or reduction in the productivity due to retention of spinnability, unpreferably occurs.

On the contrary, when the denier of the long fiber exceeds 6 d/f, the stiffness of the long fibers is increased. Thus, it becomes difficult to obtain a long fiber non-woven fabric having a sufficient softness. Further, the "metsuke" (Japanese term meaning the weight of fabric per unit area) of the long fiber non-woven fabric is preferably 5 to 50 g/m$^2$. When the metsuke is less than 5 g/m$^2$, the thickness of the long fiber non-woven fabric becomes too thin. Hence, when the long fiber fleece is fixed, when the fixed long fiber non-woven fabric is wound up, or when a short fibers are piled up or laminated with a short fiber non-woven fabric, handling of the fabric is difficult or the uniformity of the short fiber fabric is unpreferably reduced. On the other hand, when it exceeds 50 g/m$^2$, the stiffness of the long fiber non-woven fabric itself is increased and the softness is reduced.

As the long fibers which constitute the long fiber non-woven fabric, synthetic fibers formed of a thermoplastic resin, semi-synthetic fibers, and natural fibers are usable. When a raw material other than thermoplastic resins is used for long fibers, long fibers are preferred to be those soluble in a solvent since the varieties in processing conditions are broadened, for example, at the time of fixing the long fiber fleece. When long fibers are thermoplastic, the long fibers may be fibers of a single component or may be composite fibers consisting of two or more components, for example, three or four components, but two components are sufficient except for particular applications when the economy is taken into account.

As the thermoplastic resins from which the long fibers are produced, polyolefins such as polyethylene and polypropylene, polyesters, and polyamides can be mentioned, and polyolefins are particularly preferred. Composite long fibers may be non-hot-melt adhesive composite fibers or hot-melt-adhesive composite fibers. When the efficiency of fixing at contact points of long fibers with each other and the efficiency of bonding at the time of combining with short fiber non-woven fabric at a step of after-treatments are taken into consideration, hot-melt adhesive composite fibers are preferred. Hot-melt-adhesive composite long fibers refer to composite long fibers of two or more components having a low melting point component formed at least one portion of the fiber surface.

As combination examples of the components in the hot-melt-adhesive composite long fibers, the followings can be mentioned:

a high density polyethylene/polypropylene, linear low density polyethylene/polypropylene, low density polyethylene/polypropylene, copolymer or terpolymer of propylene with other polyolefin/polypropylene, linear low density polyethylene/high density polyethylene, various kind of polyethylene/thermoplastic polyester, polypropylene/thermoplastic polyester, copolymer or terpolymer of propylene with other a-olefin/thermoplastic polyester, low melting point thermoplastic polyester/thermoplastic polyester, low density polyethylene/high density polyethylene, various kinds of polyethylene/nylon 6, polypropylene/nylon 6, copolymer or terpolymer of propylene with other a-olefin/nylon 6, nylon 6/nylon 66, and nylon 6/thermoplastic polyester.

Among these combinations, polyolefin/polyolefin, and polyolefin/polyester are preferred, and their specific examples are as follows:

a high density polyethylene/polypropylene, ethylene-propylene-butene-1 crystalline terpolymer/polypropylene, and high density polyethylene/polyethylene terephthalate.

Further, among the combinations listed above, the combinations such as a polyolefin/polyolefin, for example, a high density polyethylene/polypropylene, and ethylene-propylene-butene-1 crystalline terpolymer/polypropylene are particularly preferred from the resistance to chemicals.

The melting temperature difference or softening temperature difference between a high melting point component and a low melting point component in the composite fibers is preferably 15° C. or higher. For example, when hot-melt-adhesive composite long fibers are composed of three kinds of thermoplastic resins, A, B, and C, and the melting points or softening points thereof are in the order of A>B>C, then the melting point difference or softening point difference either between A and B, or between B and C is preferably 15° C. or higher. Namely, when thermoplastic resins which constitute the hot-melt-adhesive composite long fibers are arranged in the order of from a high melting point to a low melting point or in the order of from a low melting point to a high melting point, at least one of the temperature difference or softening temperature difference between two adjacent components is preferably 15° C. or higher. When the melting points or the softening points of three kinds of thermoplastic resins which constitute the hot-melt-adhesive composite long fibers are in the order of A>B>C and only the difference between A and B is 15° C. or higher, then A is defined as high melting point component and B and C are defined as low melting point components. Further, when the melting points or softening points of three kinds of thermoplastic resins A, B and C which constitute the hot-melt-adhesive composite long fibers are in the order of A>B>C, and the melting point difference or the softening point difference is 15° C. or higher both between A and B, and between B and C, then A is defined as high melting point component and C is defined as low melting point component; and as far as the condition that the composite long fibers are hot-melt-adhesive composite long fibers is satisfied, it does not matter whether B is defined as high melting component or low melting component. This is because B is a high melting point component relative to C, but a low melting point component relative to A.

As semi-synthetic fiber or natural fiber which constitutes the long fiber non-woven fabric, rayon, cupra ammonium rayon, acetate, silk, etc. can be mentioned as examples.

As the composite long fibers, composite fibers of sheath-and-core type, eccentric sheath-and-core type, side-by-side type, multi-layer type and island-in-sea type are usable. Further, in order to impart design-forming properties and functional properties, a coloring agent, hydrophylyzing agent, (agent for making fibers hydrophilic), anti-fungus agent, etc. may be added to the long fibers. Cross-sections of the long fibers may be either circular or non-circular, and the long fibers having such a cross-section may be of hollow type or not.

Long fiber non-woven fabrics may be composed of two or more kinds of long fibers. Namely, the long fiber non-woven fabrics may be composed of a mixture of two or more kinds long fibers (filaments) such as composite fibers with single component fibers, hot-melt-adhesive composite fibers with non-hot-melt-adhesive composite fibers, single component fibers of a polymer with single component fibers of another polymer, two kinds of fibers having different cross-section, hollow fibers with non-hollow fibers, and two kinds of fibers having different denier.

Long fiber non-woven fabric may be either of a single layer or two or more layers constructed from the long fibers mentioned above.

Particularly preferable long fiber non-woven fabric in the present invention is one which contains the hot-melt-adhesive composite long fibers in a quantity of 5% by weight or more in the long fiber non-woven fabric, and the long fibers are bonded with each other by the low melting component in the hot-melt-adhesive composite long fibers. It is also possible to use a long fiber non-woven fabric which is obtained by mixing hot-melt-adhesive long fibers having a melting point lower than that of main constituent fibers by 15° C. or more, in a quantity of 5% by weight or more with the main constituent fibers, and bond the main constituent long fibers by the hot-melt-adhesive long fibers. As described, the reason for bonding the fibers with each other, for example, by hot-melt-adhesive composite long fibers or low melting point hot-melt-adhesive long fibers lies in that the bonding of the fibers is carried out not in a surface, but only at contact points, and thus the resulting long fiber non-woven fabrics have an improved hand feeling and a sufficient softness.

Long fiber non-woven fabrics having the above construction are prepared by the method, for example, as follows:

Hot-melt-adhesive composite long fibers are produced according to a known spinning process, followed by spreading the long fibers according to a static electrostatic charge method or the like, accumulating the resulting fibers on a collecting conveyer to obtain a sheet-like long fiber fleece, introducing the long fiber fleece into a space filled with a heated gas stream, and heat-treating it at the melting point or higher of that of the low melting component of the hot-melt-adhesive composite long fibers included in the long fibers but at a temperature lower than the melting point of the high melting point component, to thereby obtain the long fiber non-woven fabric. The process for fixing the long fiber fleece is not limited to the process mentioned above, that is, the hot air heating process, but known processes such as a needle-punching process, high pressure water stream process, emboss roll process, and ultrasonic heating process may be employed, and combinations of these processes may be employed. As the combinations of a fixing process of the long fiber fleece, a needle-punching treatment with an emboss roll treatment, a needle punching treatment with a supersonic heating treatment, a needle punching treatment with a hot-air heating treatment, a high pressure water stream treatment with an emboss roll treatment, a high pressure water stream treatment with a supersonic heating treatment, and a high pressure water stream treatment with a hot air heating treatment can be exemplified. These treatments may be in any order, but needle punching treatment is preferably carried out in advance in order to avoid adverse influences such as the breakage and splitting of hot-melt-adhered points formed by an emboss roll treatment, supersonic heating treatment or hot air heating treatment.

On the other hand, short fiber non-woven fabrics are obtained by accumulation and bonding of short fibers, and the denier of the short fibers is preferably 0.5 to 6 d/f. When the denier of the short fibers is less than 0.5 d/f, the needle of the spreading (opening) machine becomes difficult to pass through the fibers when the short fibers are spread, and thus only non-homogeneous short fiber non-woven fabrics having so-called nep are obtained. On the contrary, when the denier exceeds 6 d/f, the stiffness of the short fibers becomes high, hence it is impossible to obtain a short fiber non-woven fabrics having a sufficient softness.

Further, the metsuke (defined above) of the short fiber non-woven fabric is preferably 5 to 50 $g/m^2$, as in the case of the long fiber non-woven fabric. When the metsuke of the short fiber non-woven fabric is less than 5 $g/m^2$, the thickness of the short fiber non-woven fabric becomes too thin and its handling is difficult or the homogeneity of the fabric lowers as in the case of the long fiber non-woven fabric. On the contrary, when the metsuke exceeds 50 $g/m^2$, the stiffness of the short fiber non-woven fabric itself becomes high and its softness lowers. As to the short fibers, those having a fiber length of 3 to 51 mm can be used. When the fiber length of the short fibers is less than 3 mm, the bulkiness of the short fiber non-woven fabric lowers and the apparent density becomes high. On the contrary, when it exceeds 51 mm, the spreading property becomes inferior and the homogeneity lowers. In particular, those having a fiber length of 3 to 30 mm are preferable from the viewpoint of good bulkiness and homogeneity, and those of 3 to 15 mm are more preferable. As the short fibers, either of crimped fibers or not-crimped fibers may be used. In particular, from the viewpoint of good bulkiness, crimped short fibers are preferable. As to the shape of crimp, spiral type, zigzag type, and U-letter type are mentioned as examples, and spiral type and U-letter type are preferable.

Short fibers are hot-melt-adhesive composite fibers produced from various combinations of polyolefin resins such as various polyethylenes and polypropylenes, polyester resins, and polyamide resins. Hot-melt-adhesive composite short fibers refer to composite short fibers comprising two or more components, for example, three components or four components, and having a low melting point component formed on at least one portion of the fiber surface. However, two components fibers are preferable in view of economy, except for specific applications.

As to the resins used for the hot-melt-adhesive composite short fibers and the combinations thereof, it is possible to use the thermoplastic resins and their combinations described in the case of the long fibers, as they are. However, the selection thereof is carried out independently of the cases of the long fibers. In the case where three or more resin components are used, a high melting point component and a low melting point component are defined in the same manner as in the case of the long fibers. As to the hot melt-adhesive composite short fibers, it is possible to use composite fibers of sheath-and-core type, eccentric sheath-and-core type, side-by-side type, multilayer type, and island-in-sea type. Further, in order to impart design-forming properties and functional properties, a coloring agent, hydrophilyzing agent, anti-fungus agent, etc. may be added to the short fibers. Cross-sections of the hot-melt-adhesive composite short fibers may be circular or non-circular, and the hot-melt-adhesive composite short fibers having such a cross-sections may be of hollow type or non-hollow type.

The short fiber non-woven fabric may be composed by mixing two or more kinds of hot-melt-adhesive composite short fibers, in various combinations such as different type of resins, different cross-sections, hollow type and non-hollow type, different fiber length, and different deniers, selected from the hot-melt-adhesive composite short fibers produced according to the process mentioned above. The short fiber non-woven fabrics may be composed by mixing the hot-melt-adhesive composite short fibers mentioned above with hydrophilic short fibers, and the mixing ratio of the hydrophilic short fibers is 0 to 70% by weight, preferably 0 to 30% by weight based upon the weight of the short fiber non-woven fabric. The reason for adopting the mixing ratio in this range is as follows:

Repeated permeation-absorption of the body fluids becomes superior by mixing the hydrophilic fibers, but when the mixing ratio of the hydrophilic short fibers exceed 70% by weight, the ratio of the hot-melt-adhesive short fibers becomes less than 30% by weight, and as a result, the shape retention of the short fiber non-woven fabric based on the melt adhesion of the hot-melt-adhesive composite short fibers becomes difficult.

As the hydrophilic fibers referred to herein, rayon, cupra, acetate, vinylon, nylon, protein-acrylonitrile copolymer fiber, cotton, wool, silk, jute, and pulp fiber, can be exemplified, and cellulose fiber such as rayon, cupra, acetate, cotton, and pulp are particularly preferable.

Short fiber non-woven fabrics may be of a single layer or, two or more layers composed of the hot-melt-adhesive composite short fibers mentioned above, or the hot-melt-adhesive composite short fibers and the hydrophilic short fibers. When the short fiber non-woven fabrics are composed of two or more layers, the short fiber non-woven fabrics are preferred to be those having a density gradient imparted in the thickness direction of the non-woven fabric. Namely, the short fiber web are preferred to be formed such that fibers in the web are assembled so as to form a density gradient in a manner that the density is gradually increased or it is gradually reduced in the thickness direction of the web and then joined with each other. It is also preferable to impart the gradient of the mixing ratio of hydrophilic fibers in the thickness direction of non-woven fabric. That is, it is preferable to assemble and bond hydrophilic fibers in the non-woven fabrics so that their mixing ratio gradually increases or decreases in the thickness direction of the non-woven fabric. The reason for imparting the density gradient to the short fiber non-woven fabric or a gradient of the mixing ratio of the hydrophilic fibers is as follows:

Based upon the property that a liquid moves from a low density part to a high density part or from lower hydrophilic part to higher one, the penetration-absorption of the body fluid is improved, back flow after penetration-absorption is prevented, and as a result, the short fiber non-woven fabric becomes more preferable as a surface material for the absorptive article.

Importance in the present invention resides in that the short fiber non-woven fabric used for the combined non-woven fabric as the surface material is characterized in that short fiber fabric is obtained by arranging the constituent hot-melt-adhesive composite short fibers at random, and joining the fibers with each other. Namely, the short fiber non-woven fabric mentioned above is characterized in that the fabric is composed of the hot-melt-adhesive composite fibers, and the hot-melt-adhesive composite fibers are hot-melt-adhered to each other, and the crossing angle of the short fibers at at least 45%, preferably at least 50% of the total contact points in the short fiber non-woven fabric is occupied by an angle of 60° to 90° in the distribution of the crossing angle at the contact points of the short fibers. Percentage (%) of the crossing angle of 60° to 90° constitutes a scale of the randomness of the short fibers in the short fiber non-woven fabric. The percentage (%) of the crossing angle of 60° to 90° was sought by measuring the smallest angle among four angles formed with crossed and joined two short fibers, regarding this angle as crossing angle, carrying out this measurement at 100 points or more to obtain a crossing angle distribution, assuming the number of crossing angles included in crossing angles of 60° to 90° as "A", and assuming the total number of the measured crossing angles as "M", and calculating A/M×100 to obtain the percentage mentioned above. When the percentage obtained by the procedure mentioned above does not reach 45%, it is difficult to achieve the object of the present invention.

Short fiber non-woven fabric having the construction mentioned above is produced by the method, for example, as follows:

Hot-melt-adhesive composite short fibers are mixed with hydrophilic short fibers, followed by spreading the resulting fiber mixture and feeding the resulting fibers to an air-laid processing machine for non-woven fabric. Short fibers supplied to the machine are spread and scattered by the air-laid processing machine and piled up on a collecting conveyer. Multi-layer short fiber web obtained by carrying out the operation mentioned above at multi-stages is fed into a heated gas stream at a temperature from the melting point or higher of the low melting component of the hot-melt-adhesive composite short fibers to a temperature lower than the melting point of the high melting component thereof, to soften or melt the low melting component of the hot-melt-adhesive composite short fibers to thereby obtain a short fiber non-woven fabric having the short fibers bonded to each other. Conversion of the short fibers into a non-woven fabric may be carried out together with the formation of a combined fabric with a long fiber non-woven fabric. Namely, conversion of the short fibers into a non-woven fabric may be carried out by directly piling up the short fibers scattered with an air-laid processing machine on a running, long fiber non-woven fabric or a long fiber fleece, followed by heat-treating with hot air to thereby carry out the conversion of the short fibers into a non-woven fabric and formation of a combined fabric with a long fiber non-woven fabric at the same time.

The reason that the hot-melt-adhesive composite short fibers which constitute the short fiber non-woven fabric should be arranged at random lies is that a superior permeation-absorption of body fluid is obtained thereby. In the case of the short fiber non-woven fabric obtained according to an air-laid process, the constituent short fibers are arranged at random. Hence, the capillary-like function in the mechanical direction of a non-woven fabrics observed in the non-woven fabrics according to a carding process scarcely occurs, and thus the permeation-absorption of the body fluid is carried out without spreading of the body fluid in the fiber arranging direction on the surface of the non-woven fabric.

Further, since the short fibers which constitute the short fiber non-woven fabric have a sufficiently short fiber length, the fibers are arranged comparatively in the direction of the thickness of the non-woven fabric. Thus the resulting short fiber non-woven fabric exhibits:

A superior cushion property, is bulky, has a sufficiently reduced apparent density, has a capillary-like function in the thickness direction of the non-woven fabric, has an improved permeation-absorption and spot-absorption of body fluids such as urine, sweat, and blood, has a dryish feeling, and prevents back flow of permeated body fluid.

Combined non-woven fabric used as the surface material of the absorptive article is one obtained by combining at least two kinds of fabrics of the long fiber non-woven fabric and the short fiber non-woven fabric mentioned above. Combining of the long fiber non-woven fabric with the short fiber non-woven fabric may be performed either by lamination and bonding of a long fiber layer and a short fiber non-woven fabric, or by lamination and joining of a long fiber layer and a short fiber web. The long fiber layer referred to herein means a long fiber non-woven fabric or a long fiber fleece. Bonding of the long fiber layer with the short fiber layer in combining the long fiber non-woven fabric and the short fiber non-woven fabric is carried out by softening or melting the low melting point component of the hot-melt-adhesive composite short fibers contained in the short fiber layer, i.e. the short fiber non-woven fabric or the short fiber web. As specific examples, an emboss roll process, supersonic heating process, and hot air heating process can be mentioned.

In particular, in the respect of superior bulkiness, a hot air heating process is preferable for joining a long fiber layer and a short fiber layer in combining the long fiber non-woven fabric and the short fiber non-woven fabric. Further, it is preferred that a long fiber layer comprises 5% by weight or more of hot-melt-adhesive composite long fibers or a mixed low melting point hot-melt-adhesive long fibers, and the melting point of the respective low melting point components contained in the long fiber layer and the short fiber layer is lower by 15° C. or more, than the melting points of the respective high melting point components.

The reason that the melting points of the respective components in the long fiber layer and the short fiber layer are selected as described above is as follows:

Bonding of the long fiber layer with the short fiber layer in combining the long fiber non-woven fabric and the short fiber non-woven fabric is carried out not only by softening or melting the low melting point component of the hot-melt-adhesive composite short fibers contained in the short fiber layer, i.e. the short fiber non-woven fabric or the short fiber web, but also by softening or melting the low melting point component of the long fiber non-woven fabric. Even when two kinds or more of hot-melt-adhesive composite fibers are mixed in the long fiber layer or in the short fiber layer, the respective low melting components exhibit the function of hot-melt-adhesion, and can further increase the strength of the combined non-woven fabric and the bonded surface.

Hot-air heat-treatment in this case is preferably carried out at a temperature of the melting point or higher of the component having the highest melting point among the low melting point components of the long fiber layer and the short fiber layer, but at a temperature lower than the melting point of the lowest melting point component among the high melting point components of the long fiber layer and the short fiber layer.

When the hot-air heat-treatment is carried out at a temperature lower than the melting point of the component having the highest melting point among the low melting components of the long fiber layer and the short fiber layer, then the bonding of the long fiber layer and the short fiber layer at the time of combining the long fiber non-woven fabric with the short fiber non-woven fabric may sometimes be achieved with not all of the low melting components. On the contrary, when the hot-air heat treatment is carried out at a temperature higher than the melting point of the lowest melting component among the high melting components of the long fiber layer and the short fiber layer, then this high melting component causes damage or shrinkage due to heat, or reduction in the bulkiness, hence only heterogeneous composite non-woven fabrics are obtained.

When the composite non-woven fabric is provided with a density gradient or a gradient of the mixing ratio of the hydrophilic fibers in the thickness direction of the short fiber layer of the combined fabric, the short fiber layer may be made dense or coarse on the side where the long fiber non-woven fabric is bonded thereto, in accordance with the function of the member used. Further, in accordance with the function of the used member, either side of the combined non-woven fabric may be used as front surface, and a short fiber layer or a long fiber layer may further be laminated and bonded onto the thus obtained combined non-woven fabric of two layers, thereby obtaining a combined non-woven fabric of three or more layers. A sheet such as a non-woven fabric other than those mentioned above, a knitted or woven fabric, paper, and film may be laminated onto the above combined non-woven fabric of two layers or more. As described above, when a sheet such as a non-woven fabric other than the non-woven fabric mentioned above, a knitted or woven material, paper, and film is laminated onto the above composite non-woven fabric, and the surface where the sheet was further laminated is used as the surface which contacts with skin, namely as top sheet 2, the combined non-woven fabric functions as a second sheet.

A particularly preferable embodiment of combining the long fiber non-woven fabric with the short fiber non-woven fabric is a lamination and bonding of the long fiber layer and the short fiber web according to a hot-air heating process. The lamination and bonding of the long fiber layer with the short fiber web according to the hot-air heating process refer to a process of piling up the short fiber web directly on the long fiber non-woven fabric or the long fiber fleece, followed by introducing the resulting material into a heated air stream at a temperature of the melting point or higher of the low melting point component of the hot-melt-adhesive composite short fibers but a temperature lower than the melting point of the high melting point component of the composite short fiber to conduct a heat-treatment, to thereby bond the long fiber non-woven fabric with the short fiber non-woven fabric. The thus obtained combined non-woven fabric obtained by lamination and bonding of the long fiber layer and the short fiber web, i.e. the lamination and bonding of the long fiber non-woven fabric or the long fiber fleece with the short fiber web, is different from the ordinary bonded structure as in the lamination and bonding of the long fiber non-woven fabric with the short fiber non-woven fabric. That is, the short fiber web intrudes in the clearance of the long fiber non-woven fabric or the long fiber fleece on the bonded surface, whereby the adhered points of the long fibers and the short fibers are three-dimensionally formed, and a structure is provided wherein the short fibers are arranged comparatively in the thickness direction of the non-woven fabric.

Thus, the combined non-woven fabric obtained by the lamination and bonding of the long fiber layer and the short fiber web according to the hot-air heating process yields an anchor effect between the layers of the long fiber non-woven fabric and the short fiber non-woven fabric, and as a result, the absorptive article has a superior morphological stability against the slipping or dislocating stress and the twisting stress exerted from the outside, anticipated at the time of use of absorptive articles.

Since, the short fibers are arranged comparatively in the thickness direction of the non-woven fabric also between the layers of the long fiber non-woven fabric and the short fiber non-woven fabric, the resulting combined fabric is superior in the cushion property and bulkiness, sufficiently low in the apparent density, further improved in the capillary-like function in the thickness direction of the non-woven fabric, superior in the permeation-absorption and the spot-absorption of the body fluid, and reduced in the back flow of the permeated body fluid. As described above, the combination of the long fiber non-woven fabric with the short fiber non-woven fabric is preferably achieved through the lamination and bonding of the long fiber layer and the short fiber web according to the hot-air heating process from the viewpoint that the resulting combined fabric is superior in the morphological stability at the time of use, permeation-absorption and spot-absorption of the body fluid, and a small back flow of the permeated body fluid.

Even in the case of the lamination and bonding of the long fiber layer and the short fiber web according to a hot-air heating process it is preferable that the long fiber layer comprises 5% by weight or more of hot-melt adhesive composite long fibers or mixed low melting point hot-melt-adhesive long fibers layer and the melting point of the low melting point component of the long fiber layer and the short fiber layer is lower by 15° C. or more than the melting point of the respective high melting point components. The hot-air heat treatment of this case is also preferably carried out at the melting point or higher of the component having the lowest melting point among the long fiber layer and the short fiber layer, but at a temperature lower than the melting point of the component having the highest melting point among the long fiber layer and the short fiber layer. Lamination and bonding of the long fiber fleece with the short fiber web, by way of the hot-air heating, is particularly desirable, since the conversion of the long fiber fleece and the short fiber web into a non-woven fabric and their combination can simultaneously be achieved.

As described above, in the absorptive articles of the present invention, the above combined non-woven fabric is used at least as the top sheet 1 or the second sheet among the surface materials, and thus hydrophilic property is required of these sheets in order to carry out the permeation-absorption, whereas hydrophobic property is generally required of other surface materials. Imparting of hydrophilic property or water-repellency to the combined non-woven fabrics can be achieved according to known procedures such as coating, adhesion, or incorporation of a chemical agent, and this is preferable under the conditions where the advantageous effects of the present invention are not impeded to exhibit.

Back sheet 3 has no particular limitation as far as it has a sufficient non-permeability of the fluids, and a knitted or woven fabric, non-woven fabric, and film are exemplified. It is preferably a liquid impermeable but steam-permeable sheet obtained by adding a filler such as calcium carbonate to a thermoplastic resin, followed by extruding the resin to form a film and stretching the film. It is more preferably a material having a feeling close to skin, for example, a combined material of the above film with a non-woven fabric or a knitted or woven fabric.

Further, a combined material comprising the combined non-woven fabric mentioned above with a non-woven fabric other than the non-woven fabric, a film, or a knitted or woven fabric may be used.

Absorbing body 4 is composed mainly of hydrophilic fibers and a high molecular absorbing body (Super Absorption Polymer). As the hydrophilic fibers referred to herein, rayon, cupra, acetate, vinylon, nylon, protein-acrylonitrile copolymer fiber, cotton, wool, silk, jute, and pulp are mentioned, and cellulose fiber such as rayon, cupra, acetate and pulp are preferable. Practically, however pulp has been used in most cases. Pulp fibers have no particular limitation as far as they are those used so far as an absorbing body, but usually the average fiber length of the pulp fibers is preferably in the range of 0.8 to 5 mm, taking crushing, lamination, and compression treatment into account.

As mentioned above, while the high molecular absorbing body has no particular limitation as far as it is a product used so far, the saturated absorption quantity of the absorbing body is preferably 25 g/g or more, and those of fiber-shape or particle-shape are usable. Saturated absorption quantity is determined by introducing 1 g of a sample high molecular absorbing body into a tea pack made from 250 mesh nylon, immersing it in an excess quantity of 0.9% by weight of aqueous salt solution for one hour, draining for 15 minutes, and calculating the increased weight which is defined as saturated absorption.

When the high molecular absorbing body is in the shape of a particle, the particle diameter is preferably 100 to 800 $\mu$m. Specific high molecular absorbing bodies preferably include sodium polyacrylate, acrylic acid-vinyl alcohol copolymer, cross-linked sodium polyacrylate, starch-acrylic acid graft copolymer, isobutylene-maleic acid an hydride copolymer or its saponified substance, potassium polyacrylate, and cesium polyacrylate. Blending ratio of the high molecular absorbing body is preferably in the range of 25 to 85% by weight based upon the total weight of the absorbing body, and these high molecular absorbing bodies are usable alone or in a mixture. Further, it is also preferred to blend hot-melt-adhesive composite short fibers with the absorbing body. The blending ratio of the hot-melt adhesive composite short fibers is preferably 0 to 60% based upon the total weight of fibers used for the absorbing body. The reason for the preferred blending of the hot-melt-adhesive composite short fibers is as follows:

When hot-melt-adhesive composite short fibers are heat-treated, a network wherein hot-melt-adhesive composite short fibers are bonded to the whole absorbing body is formed, and thus an effect of the morphological stability against the compression, dislocating stress, and twisting stress caused by the movement of a consumer is exhibited to thereby prevent reduction in the body fluid-absorption with the absorbing body.

In general, the absorbing body is covered with a wrapping material 8 for shape retention and so-called prevention of powder falling off. Wrapping material 8 is composed mainly of hydrophilic short fibers such as rayon, cupra, acetate, vinylon, nylon, protein-acrylonitrile copolymer fiber, cotton, wool, silk, jute, and pulp, and is preferably cellulose fibers such as rayon, cupra, acetate, and pulp. However, pulp has practically been used in most cases. While thermoplastic composite short fibers can be blended with wrapping material 8, its blending ratio is preferably 0 to 60% based upon the total weight of fibers used for the absorbing body. The reason for preferably blending the hot-melt-adhesive composite short fibers is as follows:

When hot-melt-adhesive composite short fibers are heat-treated in the same manner as in the case of the absorbing body, a network wherein the hot-melt-adhesive composite short fibers are bonded to the whole of the absorbing body is formed, and an effect a morphological stability against compression, dislocating stress, and twisting stress caused by movement of a consumer is exhibited to thereby prevent reduction in the body fluid absorption, and further, at the time of hot-melt-adhesion with a surface material such as top sheet 2 and back sheet 3 according to a heated roll process or super-sonic heating process, strong adhesion points are formed to thereby afford a superior morphological stability as the whole of the absorptive article.

As the hot-melt-adhesive composite short fibers used for the absorbing body and the wrapping material, those disclosed in the case of short fibers used for the combined non-woven fabric of the surface material can be used, and the selection thereof is carried out independently of the case of the short fibers. Hot-melt-adhesive composite short fibers may be those consisting of two or more, for example, 3 or 4 components. However, two component fibers are sufficient except for specific applications, taking economy into consideration. Cut length of the hot-melt-adhesive composite short fibers is in the range in which they can be formed into a sheet-like material. Whereas it has no particular limitation, it is preferably 3 to 90 mm.

It is also preferred to use an absorbing layer wherein the wrapping material 8 and the absorbing body 4 are integrated together, in place of both of the wrapping material 8 and the absorbing body 4. Absorbing layer wherein the wrapping material 8 and the absorbing body 4 are bonded and integrated together, referred to herein, means a material obtained by placing the above absorbing body 4 between non-woven fabrics prepared by blending 0 to 60% of the hot-melt-adhesive composite short fibers mentioned above with the above hydrophilic short fibers, followed by bonding to integrate, and integrally cutting the resulting material into a desired shape. For example, the absorbing layer mentioned above is produced by the method as follows:

According to air-laid process, a blend of the above hydrophilic short fibers with 0 to 60% of the above hot-melt-adhesive composite short fibers is spread, scattered and piled up, followed by successively spreading, scattering and piling up a mixture of the above hydrophilic fibers with the above high molecular absorbing body thereon, further spreading, scattering and piling up a blend of the hydrophilic short fibers with 0 to 60% of the above hot-melt-adhesive composite short fibers thereon, bonding to integrate by a heat-treatment, and integrally cutting. Bonding in the integration of the wrapping material 8 and the absorbing body 4 is carried out by softening or melting the low melting point component of the hot-melt-adhesive composite short fibers contained in the short fiber web, and as specific examples, an emboss roll process, supersonic heating process, and hot air-heating process are mentioned. Among these processes, the hot air heating process is preferred in that uniform adhesion points are formed between the respective hot-melt-adhesive composite short fibers of the whole absorber. Further, for stronger bonding, it is also preferred to blend the hot-melt-adhesive composite short fibers mentioned above with the absorbing body 4 of the absorbing layer obtained by integrating the above wrapping material 8 and the absorbing body 4. Such absorbing layer is a preferable embodiment in that powder-falling off from the absorbing body is scarce and the handling is easy at the time of processing fibers into an absorptive article.

In general, the absorptive articles absorb a large quantity of body fluids at the point which contacts with the exit of the body fluids, and the absorbing body falls in a state saturated with the fluids. The body fluids spread radially from that point and causes wetting from the part nearest to the legs, that is, so-called lateral leakage. As one of preferable countermeasures for preventing the lateral leakage, it is possible to place a body fluid-diffusing layer 10 between the top sheet 2 and the absorbing body 4. The body fluid-diffusing layer 10 rapidly absorbs and diffuses the body fluids and causes the absorption of the body fluids with the whole of the absorbing body to thereby increase the total absorption quantity of the body fluids. As the body fluid-diffusing layer 10, a knitted or woven fabric, fiber assembly, and porous film are exemplified, and practically the fiber assembly is generally used. Fiber assembly referred to herein means a fiber assembly such as a short fiber web, long fiber fleece, and sliver, and a non-woven fabric such as a short fiber non-woven fabric, long fiber non-woven fabric, and melt-blown non-woven fabric obtained by forming the above fiber assembly into a cloth.

Body fluid-diffusing layer 10 is preferably hydrophilic from the viewpoint that the layer 10 develops a good transporting property and diffusing property of the body fluids. Body fluid-diffusing layer 10 can be treated so as to have hydrophilic property by coating or adhering a hydrophilyzing agent (agent for imparting hydrophilic property) such as a surfactant or the like on the surface. In particular, in the case where the body fluid-diffusing layer 10 is composed of a thermoplastic resin, a hydrophilyzing agent such as a hydrophilyzing resin or a surfactant is incorporated into a thermoplastic resin, followed by molding it into fibers or a film to make the body fluid-diffusing layer 10 hydrophilic in advance. As the hydrophilyzing resin, a homopolymer of ethers such as ethylene glycol or vinyl alcohol, and copolymers thereof with ethylene or propylene, and polyether block amide copolymer are exemplified. As specific examples, thermoplastic polyethylene glycol (Trade name: Aquacoke; made by Sumitomo Seika Co., Ltd.), ethylene-vinyl alcohol copolymer (Trade name: Eval, made by Kuraray Co., Ltd.), and polyether block amide copolymer (Trade name: PEBAX, made by ATOCHEM corporation) are mentioned. The percentage (%) of the polymer to be added in the case where a hydrophilyzing resin is incorporated into a thermoplastic resin as a main substance is preferably 20 to 100%. The hydrophilyzing resin can be adequately selected from the resins and added singly or as a mixture of two or more kinds of resins. As the surfactant, anionic surfactants such as higher alcohol sulfuric acid ester salts, alkylbenzene sulfonic acid salts, and higher alcohol phosphoric acid ester salts, cationic surfactants such as alkylamine salts and quaternary amine salts, and nonionic surfactants such as polyoxyethylenes, polyoxyethylene alkyl ethers, polyoxyethylene alkyl esters, and polyvalent alcohol alkyl esters are mentioned. The percentage (%) of the surfactant to be added in the case where the surfactant is incorporated into the thermoplastic resins as the main substance is preferably 0.05 to 10.0% by weight. The surfactant is selected from the above kinds and added singly or as a mixture of two or more kinds. Further, a hydrophilyzing agent such as surfactants may be coated or adhered onto the surface of fibers or film having a hydrophilyzing agent such as a resin and surfactant incorporated therein.

As the fibers from which the knitted or woven fabric, or the non-woven fiber aggregate used for the body-fluid-diffusing layer 10 is formed, short fibers or long fibers (filaments) can be used, and the short or long fibers having a fineness of 0.5 to 18 d/f are usable. When the fineness of the fibers is less than 0.5 d/f, reduction in the spinnability due to a high speed spinning for maintaining a high productivity or reduction in the productivity for retaining the spinnability is caused. On the contrary, when the fineness exceeds 18 d/f, the stiffness of the fibers becomes high, and hence a non-woven fiber aggregate having a sufficient softness cannot be obtained. The metsuke of the non-woven fiber aggregate is preferably 5 to 150 g/m². When the metsuke of the non-woven fiber aggregate is less than 5 g/m², the thickness becomes too small, hence its handling at the time of molding into an absorptive article is difficult and the homogeneity of the article lowers. On the contrary, when the metsuke exceeds 150 g/m², the stiffness of the non-woven fiber aggregate becomes high and the softness lowers.

As the fibers which constitute the knitted or woven fabric or the non-woven fiber aggregate, those disclosed in the case of long fibers used for the combined non-woven fabric of the surface material are usable, and the selection thereof is carried out independently of the case of long fibers. In the case where the fibers are thermoplastic, the fibers may be those consisting of one resin component or composite fibers comprising two or more components, for example, three or four resin components. However, two components are sufficient except for specific applications, taking economy into account.

As the fibers which constitute a knitted or woven fabric, or a non-woven fiber aggregate, crimped fibers and non-crimped fibers are usable. However, crimped fibers are preferred in that the fibers have a superior bulkiness and excellent in low back flow. As the form of crimps, those of spiral type, zig-zag type, and U-letter type are mentioned, and those of spiral type and U-letter type are preferred. As fibers which constitute the knitted or woven fabric, or non-woven fiber aggregate, composite fibers of sheath-and-core type, eccentric sheath-and-core type, side-by-side type, multilayer type, and island-in-sea type are usable. In order to impart a design-forming property and a functional property, a coloring agent, and anti-fungus agent may be added to the fibers. The cross-section of the fibers may be circular or not-circular, and the fibers having such a cross-section may be of hollow type or not. In particular, in order to develop a good transport property and diffusing property of the body fluids, the fiber cross-section is preferably non-circular.

The extent of non-circular of the cross-section is preferably 1.3 or more. The non-circular extent is calculated by the equation:

$$L/(2\sqrt{(\pi S)})$$

wherein L is the circumferential length of the fiber having a non-circular cross-section and S is the cross-sectional area of the fiber having the non-circular cross-section.

Knitted or woven fabric, or the non-woven fiber aggregate used as the body fluid-diffusing layer 10 may be composed by mixing two or more kinds of fibers in the following various combination:

Long fibers with short fibers, short fibers having different fiber lengths, composite fibers with single component fibers, different resin combinations in the case of composite fibers, hot-melt-adhesive fibers with non-hot-melt-adhesive fibers in the case of composite fibers, different resins in the case of single component fibers, different cross-sections or different non-circular extent, hollow fibers with non-hollow fibers, fibers added with an additive agent such as a hydrophilyzing agent and anti-fungus agent with fibers added with no such additive, fibers with different additives, fibers with different fiber lengths, and fibers with different fineness.

Knitted or woven fabric, or non-woven fiber aggregate used as the body fluid-diffusing layer may be of a single layer, or two or more layers composed of the fibers mentioned above.

Body fluid-diffusing layer 10 is introduced between top sheet 2 and absorbing body 4. In the case where the absorbing body 4 is covered with wrapping material 8, the body fluid-diffusing layer 10 may be introduced between top sheet 2 and wrapping material 8 or may be introduced between wrapping material 8 and absorbing body 4. In particular, in order to avoid the clogging of body fluid-diffusing layer 10 at the time of bonding with a hot-melt-adhesive, the body fluid-diffusing layer 10 is preferably introduced between the wrapping material 8 and the absorbing body 4.

Figure 2:
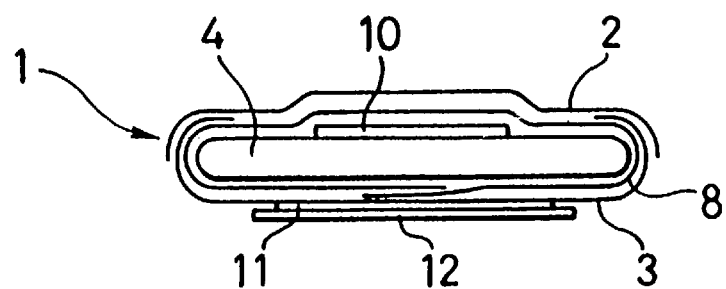

As an embodiment other than sanitary napkin 1 shown in FIGS. 1 and 2, in the present invention, a pair of wings or a pair of side gathers or the both are preferably provided on the sanitary napkin 1. The wings may be formed by extending the top sheet 2 and the back sheet 3 from the vicinity of the center of side part 7 in lengthwise direction side part 7 of the absorptive article, or may be formed by bonding a member other than top sheet 2 and back sheet 3 to the vicinity of the center of side part 7 in lengthwise direction. In this case, the wings, when used, are fitted so as to be folded back under the panties and wrap the panties therein. At least two effects can be achieved by such arrangement. The first effect is that a double barrier is constructed particularly at the end part of the panties whereby a consumer and panties can be prevented from being dirtied with the body fluid such as blood. The second effect is that the napkin is kept at an adequate position by means of the adhesive layer provided on the surface of the wings at the side of the panties. Side gathers are formed along the lengthwise direction of the absorptive article under a state where they are protruded upwards from top sheet 2 at the slightly inner side of the lengthwise side part of the absorber 7, or the protruded part is folded inside. Side gathers are provided in order to prevent the lateral leakage of the body fluid, and in order to effect this function, the side gathers are liquid-impermeable as in the case of back sheet 3.

Bonding between the respective members such as top sheet 2 and back sheet 3, wrapping material 8, absorbing body 4, body fluid-diffusing layer 10, wings, and side gathers, is carried out by means of a hot-melt-adhesive, other adhesives, or tackiness agent, or by hot-melt-adhesion according to a heating roll process, supersonic heating process, etc. Further, as the adhesion layer 11 provided on the back sheet 3 or as the adhesion layer provided on the surface of wings at the side of panties, a hot-melt-adhesive and other adhesives, and tackiness agent are used. Adhesion layer 11 is covered with release liner 12 in order to protect the adhesion layer or other purposes.

EXAMPLES

The present invention will be described in more detail with reference to Examples. The definitions of the physical parameters of absorptive articles in Examples and the methods for determining the parameters are as follows:
(Metsuke)

Weight of a sample non-woven fabric is divided by its area and the metsuke is expressed by weight (g) per 1 m² of the non-woven fabric.
(Shear Strength)

Morphological stability of a composite non-woven fabric against the dislocating stress and twisting stress exerted when the absorptive article is used as a surface material of an absorptive article was evaluated as shear strength. A sample composite non-woven fabric was cut to a size of 5 cm wide and 15 cm long, followed by peeling off the long fiber layer from the short fiber layer by a length of 6.5 cm from both ends in the lengthwise direction to provide a sample wherein only a central 2 cm portion has a structure of combined non-woven fabric. This sample was subjected to a tensile test by means of a constant speed tensile tester, wherein the long fiber non-woven fabric is gripped on one hand and the short fiber non-woven fabric is gripped on the other hand, and the tensile test was carried out till breakage of the sample fabric. The broken state of the broken sample was observed. The shear strength was expressed by the following symbols:

∘: Fabric which was broken.

Δ: Fabric wherein the long fiber layer was not clearly separated from the short fiber layer.

×: Fabric wherein the long fiber layer was clearly separated from the short fiber layer.

(Surface Hand Feeling)

Feeling such as skin contact feeling was evaluated as surface hand feeling according to contact feeling by 10 monitors. As to the testing method, monitors grasped a sample by fingers and recorded whether or not they felt that it was soft or had a good feeling, and a sample recorded to be a material which was soft or had a good feeling was given one point/one person.

(Apparent Density)

When a load of 2.0 g/cm$^2$ was added to the range of 35 mmφ of a sample, using Digithickness tester made by Toyo Seiki Co., Ltd., the resulting thickness was assumed as D mm, and when the metsuke of the sample was assumed as Mg/m$^2$, then the apparent density was calculated by the equation of M/(D×1000), and its unit is g/cm$^3$.

(Extent of Not-Circular Cross-Section)

Extent of not-circular cross-section was calculated by the following equation:

$$L/(2\sqrt{(\pi S)})$$

wherein L is the circumferential length of a sample fiber having a non-circular cross-section and S is the cross-sectional area of the sample fiber.

(Permeation Speed)

A cylinder of 30 mmφ, a thickness of 4 mm and a weight of 50 g was placed on a top sheet of a sample combined non-woven fabric, followed by feeding 50 ml of physiological saline into the cylinder in one breath, and determining the period of time since the feeding till the solution was absorbed in the sample. The period of time was regarded as permeation speed.

(Exudation Property)

Spot absorption was evaluated in terms of exudation property.

After the determination of the permeation speed, the distance between two boundaries opposite to each other on the surface of the sample fabric, and where traces of physiologic saline spread in the sample were longest was assumed as L, and the value calculated by the equation (L−50)/50 was regarded as exudation property.

(Back Flow Property)

After the determination of the permeation speed, the sample fabric was allowed to stand for 3 minutes, and a filter paper was placed on the sample fabric. Weight of the physiologic saline absorbed by the filter paper when a load of 5 kg was added on the filter paper for 30 seconds was regarded as back flow property.

(Random Property)

With the short fiber layer of a sample combined non-woven fabric, the smallest angle among the squares formed by bonded crossing two short fibers was determined, and regarded as crossing angle. This determination was carried out at 100 points or more, followed by seeking a crossing angle distribution. The number of the crossing angles included in the range of crossing angles of 60° to 90° was assumed as A, and the total number of determined crossing angles was assumed as M. Then, the value calculated by the equation, A/M×100 was regarded as random property.

Example 1

A polypropylene resin was heated to melt followed by introducing it into a melt-spinning apparatus and spinning long fibers. Immediately after the spinning, the long fibers were stretched so as to produce long fibers having a fineness of 2 denier. Stretched long fibers were spread into individual fibers according to an electrostatic charge process, then piled up on a collecting conveyer to obtain a long fiber fleece. This long fiber fleece was fed between a roll heated to 152° C. and having many point-like projected parts and a flat roll heated alike to obtain a long fiber non-woven fabric having a metsuke of 14 g/m$^2$. This long fiber non-woven fabric was fed onto a collecting conveyer of an air-laid type processing machine for non-woven fabric. On the other hand, hot-melt adhesive composite short fibers having a polypropylene resin as a core component and a high density polyethylene resin as a sheath component, a fineness of 2 deniers, and a cut length of 10 mm were spread, and fed to an air-laid processing machine. The short fibers supplied were spread and scattered by means of the air-laid type processing machine, piled up on the long fiber non-woven fabric fed onto a collecting conveyer mentioned above to obtain a laminated product of the long fiber non-woven fabric and a short fiber web. Metsuke of the short fiber web was 12 g/m$^2$. The laminated product of the long fiber non-woven fabric and the short fiber web was introduced into a heated air stream at 138° C. to melt the high density polyethylene resin which is a low melting point component of the hot-melt adhesive composite short fibers to bond the short fibers to each other, and to bond the long fiber layer with the short fiber layer to obtain a combined non-woven fabric.

Using this combined non-woven fabric as top sheet, an absorptive article was prepared.

Example 2

A polypropylene resin and a high density polyethylene resin were melted, followed by introducing the melt into a melt-composite spinning apparatus, and spinning hot-melt-adhesive composite long fibers composed of the polypropylene resin as a core component and the high density polyethylene resin as a sheath component. Immediately after the spinning, the long fibers were stretched so as to give hot-melt-adhesive composite long fibers having a fineness of 2 denier. The stretched hot-melt-adhesive composite long fibers were spread into individual fibers according to an electrostatic charge process, then piled up on a collecting conveyer to obtain a hot-melt-adhesive composite long fiber fleece having a metsuke of 14 g/m$^2$. This long fiber fleece was fed, as it is, onto a collecting conveyer of an air-laid type processing machine. On the other hand, hot-melt-adhesive composite short fibers composed of a polypropylene resin as a core component and a high density polyethylene resin as a sheath component, and having a fineness of 2 deniers and a cut length of 10 mm were spread and fed into an air-laid type processing machine. The short fibers supplied were spread into individual fibers and scattered by means of the air-laid-processing machine, and piled upon the long fiber fleece fed to the collecting conveyer mentioned above to obtain a laminated product of the long fiber fleece and the short fiber web. Metsuke of the short fiber web was made to be 12 g/m$^2$. The laminated product of the long fiber fleece and the short fiber web was introduced into a heated gas stream at 138° C. to melt the high density polyethylene resin as the low melting component of the hot-melt-adhesive composite short fibers and thereby bond the respective short fibers with each other, the long fibers with each other, and the long fiber layer and the short fiber layer with each other, to obtain a combined non-woven fabric. Using this combined non-woven fabric as the top sheet, an absorptive product was prepared.

Example 3

A composite non-woven fabric was prepared under the same conditions as in Example 2 except that the cut length of the short fiber in the non-woven fabric was made 5 mm. Using this combined non-woven fabric as the top sheet, an absorptive article was prepared.

Example 4

A composite non-woven fabric was prepared under the same conditions as in Example 2 except that the cut length of the short fiber in the non-woven fabric was made 30 mm. Using this combined non-woven fabric as the top sheet, an absorptive article was prepared.

Example 5

A composite non-woven fabric was prepared under the same conditions as in Example 2 except that the cut length of the short fiber in the non-woven fabric was made 51 mm. Using this composite non-woven fabric as the top sheet, an absorptive article was prepared.

Example 6

A composite non-woven fabric was prepared under the same conditions as in Example 3 except that rayon fibers having a fineness of 3 denier and a cut length of 6 mm were mixed in the short fiber layer, in a quantity of 30% by weight. Using this combined non-woven fabric as the top sheet, an absorptive article was prepared.

Example 7

A composite non-woven fabric was prepared under the same conditions as in Example 3 except that rayon fibers having a fineness of 3 denier and a cut length of 6 mm were mixed in the short fiber layer, in a quantity of 70% by weight. Using this combined non-woven fabric as the top sheet, am absorptive article was prepared.

Example 8

Short fibers formed from a polypropylene resin, having 6.0 weight % of a non-ionic surfactant, sorbitan palmitic acid monoester (Trade name: Span 40, made by ICI, America) incorporated therein, having a fineness of 2 denier, and having a cut length of 45 mm were introduced into a parallel roller carding machine, and spread into individual fibers to obtain a short fiber web having a metsuke of 48 g/m$^2$. This short fiber web was subjected to a treatment with high pressure water streams to prepare a body fluid-diffusing layer. This body fluid-diffusing layer was placedbetween a wrapping material 8 and an absorbing body 4, and using the combined non-woven fabric prepared in Example 3, as a surface material, an absorptive article was prepared.

Example 9

Hot melt-adhesive composite short fibers formed from a polypropylene resin and a low density polyethylene resin, and having 0.3% by weight of a surfactant adhered on the surface, and having a fineness of 2 denier and a out length of 64 mm were introduced into a parallel roller carding machine and spread into individual fibers to obtain a short fiber web having a metsuke of 62 g/m$^2$.

This short fiber web was subjected to a hot air heating treatment to prepare a body fluid-diffusing layer. This body fluid-diffusing layer was placed between wrapping material 8 and absorbing body 4, and using the combined non-woven fabric prepared in Example 3 as a surface material, an absorptive article was prepared.

Example 10

Hot-melt-adhesive composite short fibers formed from a polypropylene resin and a high density polyethylene resin, and having 0.8% by weight of a surfactant adhered on the surface, and having a fineness of 2 denier and a cut length of 64 mm were mixed with rayon short fibers having 0.3% by weight of a surfactant adhered onto the surface, and having a fineness of 4 denier and a cut length of 51 mm, followed by introducing the mixture into a parallel roller carding machine and spreading it into individual fibers to obtain a short fiber web having a metsuke of 70 g/m$^2$. This short fiber web was subjected to a hot air heating treatment to prepare a body fluid-diffusing layer. This body fluid-diffusing layer was placed between a wrapping material 8 and an absorbing body 4, and using the combined non-woven fabric prepared in Example 3 as a surface material, an absorptive article was prepared.

Example 11

Short fibers formed from a polypropylene resin and having 20% by weight of a hydrophilic resin incorporated therein, and having a fineness of 3 denier and a cut length of 76 mm were mixed with short fibers formed from a PET resin, and having 0.3% by weight of a surfactant adhered onto the surface thereof, and having a fineness of 10 denier and a cut length of 89 mm, followed by introducing the mixture into a parallel roller carding machine and spreading into individual fibers to obtain a short fiber web having a metsuke of 146 g/m$^2$. This short fiber web was placed, as it is, and as a body fluid-diffusing layer, between a wrapping material 8 and an absorbing body 4, and using the combined non-woven fabric prepared in Example 3 as a surface material, an absorptive article was prepared. Hydrophilic resin used in this Example and Example 12 was the ethylene-vinyl alcohol copolymer containing 44 mol % of ethylene unit, and having a melting point of 164° C. and MI (190° C.) of 5.5 (Eval, EP-E 015, produced by Kuraray Co. Ltd.).

Example 12

Hot melt-adhesive composite short fibers formed from a polypropylene resin and a high density polyethylene resin, having 60% by weight of a hydrophilic resin incorporated therein and 0.3% by weight of a surfactant adhered on their surface, and having a fineness of 3 denier and a cut length of 64 mm were mixed with short fibers formed from a PET resin, having 0.4% by weight of a surfactant adhered on their surface, and having a fineness of 8 denier and a cut length of 89 mm. The mixture was introduced into a parallel roller carding machine and spreading into individual fibers to obtain a short fiber web having a metsuke of 35 g/m². The short fiber web was subjected to a hot air heat treatment to prepare a body fluid-diffusing layer. This body fluid-diffusing layer was placed between wrapping material 8 and absorbing body 4, and using the combined non-woven fabric prepared in Example 3 as a surface material, an absorptive article was prepared.

Example 13

Hot-melt-adhesive composite short fibers formed from a polypropylene resin and a high density polyethylene resin, having 0.2% by weight of a surfactant incorporated therein, and having a fineness of 3 denier and a cut length of 51 mm were mixed with short fibers formed from a PET resin, having 0.5% by weight of a surfactant adhered onto the surface, and having fineness of 6 denier and a cut length of 89 mm, followed by introducing the mixture into a parallel carding machine and spreading into individual fibers to obtain a short fiber web having a metsuke of 146 g/m². This short fiber web was subjected to a needle-punching treatment to prepare a body fluid-diffusing layer. This body fluid-diffusing layer was placed between wrapping material 8 and absorbing body 4, and using the combined non-woven fabric prepared in Example 3 as a surface material, an absorptive article was prepared.

Example 14

Long fibers formed from a polypropylene resin and having a fineness of 2 denier were mixed with long fibers formed from a polypropylene resin and having spiral crimps, followed by introducing the mixture into an air sucker and spreading into individual fibers to obtain a long fiber fleece having a metsuke of 95 g/m². This long fiber fleece was applied with a surfactant in an amount of 0.3% by weight onto the surface and was dried. This long fiber fleece was placed, as it was, and as a body fluid-diffusing layer, between wrapping material 8 and absorbing body 4, and using the combined non-woven fabric prepared in Example 3 as a surface material, an absorptive article was prepared.

Example 15

A melt-blown non-woven fabric having a metsuke of 85 g/m² and comprising fibers having a fineness of 0.35 denier formed from a polypropylene resin and having 9.8% a by weight of a surfactant incorporated therein was placed, as a body fluid-diffusing layer, between wrapping material 8 and absorbing body 4, and using the combined non-woven fabric prepared in Example 3 as a surface material, an absorptive article was prepared.

Comparative Example 1

A polypropylene resin was melted and introduced into a melt-spinning apparatus to spin long fibers. Immediately after the spinning, the long fibers were stretched so as to give long fibers having a fineness of 2 denier, spreading into individual fibers according to an electrostatic charge process, then piled up on a collecting conveyer to obtain a long fiber fleece. This long fleece was introduced between a roll having a number of point-like projections heated to 152° C. and a flat roll heated as above to obtain a long fiber non-woven fabric having a metsuke of 14 g/m².

Hot-melt-adhesive composite short fibers formed from a polypropylene resin as a core component and a high density polyethylene resin as a sheath component, and having a fineness of 2 denier and cut length of 64 mm were introduced into a parallel roll carding machine and spread into individual fibers to obtain a short fiber web having a metsuke of 12 g/m². This short fiber web was introduced into heated air stream at 138° C. to melt the high density polyethylene as a lower melting component in the hot-melt-adhesive composite short fibers and to bond the respective short fibers to each other to obtain a short fiber non-woven fabric. The thus obtained long fiber non-woven fabric and short fiber non-woven fabric were laminated, followed by introducing the laminate into a heated air stream at 138° C. to melt the high density polyethylene as a lower melting component of the hot-melt-adhesive composite short fibers and bond the long fiber layer with the short fiber layer to obtain a combined non-woven fabric. Using this combined non-woven fabric as a top sheet, an absorptive article was prepared.

Comparative Example 2

A polypropylene resin was melted and introduced into a melt-spinning apparatus and spun into long fibers.

Immediately after the spinning, the long fibers were stretched so as to give fibers having a fineness of 2 denier, spread into individual fibers according to an electrostatic charge process, and piled up on a collecting conveyer to obtain a long fiber fleece. This long fiber fleece was introduced between a roll having a number of point-like projections heated to 152° C., and a flat roll heated as above to obtain a long fiber non-woven fabric having a metsuke of 14 g/m². This long fiber non-woven fabric was supplied onto a conveyer of a hot-air heating type processing machine.

Hot-melt-adhesive composite short fibers formed from a polypropylene resin as a core component and a high density polyethylene as a sheath component, and having a fineness of 2 denier and a cut length of 64 mm were introduced into a parallel roll carding machine, and spread into individual fibers to obtain a short fiber web having a metsuke of 12 g/m². This short fiber web was laminated onto the long fiber non-woven fabric supplied onto a conveyer of the hot air heating type processing machine mentioned above to obtain a laminate of the long fiber non-woven fabric and the short fiber web. The laminate of the long fiber non-woven fabric and the short fiber web was introduced into a heated air stream at 138° C. to melt the high density polyethylene as a low melting component of the hot-melt-adhesive composite short fibers and to bond the short fibers to each other, and the long fiber layer with the short fiber layer to obtain a combined non-woven fabric. Using this combined non-woven fabric as a top sheet, an absorptive article was prepared.

Comparative Example 3

A combined non-woven fabric was prepared under the same conditions as in comparative Example 2 except that the short fiber web-forming machine was replaced by a random roller carding machine. Using this combined non-woven fabric as a top sheet, an absorptive article was prepared.

Comparative Example 4

A combined non-woven fabric was prepared under the same conditions as in Comparative Example 2 except that the short fiber web forming machine was changed to a random webber. Using the composite non-woven fabric as a top sheet, an absorptive article was prepared.

Comparative Example 5

A polypropylene resin and a high density polyethylene resin were melted, introduced into a melt-composite spinning apparatus, and extruded to form hot-melt-adhesive composite long fibers comprising the polypropylene resin as a core component and the high density polyethylene resin as a sheath component. Immediately after the spinning, the long fibers were stretched so as to give hot-melt-adhesive composite long fibers having a fineness of 2 denier, followed by spreading the stretched hot-melt-adhesive composite long fibers into individual fibers according to an electrostatic charge process, and piling up the resulting fibers on a collecting conveyer to obtain a hot-melt-adhesive composite long fiber fleece having a metsuke of 14 g/m². This long fiber fleece was fed, as it was, to a collective conveyer of an air-laid type processing machine.

Hot-melt-adhesive composite short fibers formed from a polypropylene resin used as a core component and a high density polyethylene resin used as a sheath component, and having a fineness of 2 denier and a cut length of 64 mm were introduced into a parallel roll carding machine and spread into individual fibers to obtain a short fiber web having a metsuke of 12 g/m². This short fiber web was laminated onto the long fiber non-woven fabric supplied onto the conveyer of a hot air heating type processing machine mentioned above, to obtain a laminated product of the long fiber non-woven fabric and a short fiber web. This laminated product was introduced into a heated air stream at 138° C., followed by melting the high density polyethylene as a low melting component of the hot-melt-adhesive composite short fibers, and thereby bonding the short fibers to each other and the long fiber layer with the short fiber layer to obtain a combined non-woven fabric. Using this combined non-woven fabric as a top sheet, an absorptive article was prepared.

Comparative Example 6

A combined non-woven fabric was prepared under the same conditions as in Example 2 except that the cut length of the short fibers of the non-woven fabric was changed to 64 mm. Using this combined non-woven fabric as a top sheet, an absorptive article was prepared.

The results of determination of shear strength, surface hand feeling, apparent density, permeation speed, exudation property, back flow property and random property of the absorptive articles prepared in the Examples and Comparative Examples mentioned above are shown in Tables 1, 2 and 3. As to the absorbing bodies used in Examples and Comparative Examples, a commercially available paper diaper (Trade name: Merries, made by Kao Corp.) was decomposed to find the composition of the absorbing body, and the same material as the commercial one was used in Examples and Comparative Examples.

TABLE 1-1

| | | | | Example | | |
|---|---|---|---|---|---|---|
| | | | | 1 | 2 | 3 |
| Surface material | Long fiber layer | Long fiber | Type of fiber | Single type | Hot-melt-adhesive composite type | Hot-melt-adhesive composite type |
| | | | Used resin | PP | PP/HDPE | PP/HDPE |
| | | | Denier | 2 d | 2 d | 2 d |
| | | Metsuke (g/m²) | | 14 | 14 | 14 |
| | | Long fiber fleece-fixing method | | Emboss roll process | — | — |
| | Short fiber layer | Hot-melt-adhesive composite short fiber | Used resin | PP/HDPE | PP/HDPE | PP/HDPE |
| | | | Crimp | Spiral type | Spiral type | Spiral type |
| | | | Denier × cut length | $2^4 \times 10$** | $2^{-4} \times 10$** | $2^4 \times 5$** |
| | | Hydrophilic short fiber | Mixing ratio (wt. %) | 0 | 0 | 0 |
| | | | Material | — | — | — |
| | | | Denier × cut length | — | — | — |
| | | Web-forming process | | Air-laid process | Air-laid process | Air-laid process |
| | | Metsuke (g/m²) | | 12 | 12 | 12 |
| | | Short fiber web-fixing | | — | — | — |
| | | Combining method | | Hot air-heating process | Hot air-heating process | Hot air-heating process |
| Composite non-woven | | Shear strength | | Δ | ○ | ○ |
| | | Surface feeling | | 8 | 10 | 10 |
| | | Apparent density (g/cm³) | | 0.037 | 0.031 | 0.032 |
| Permeation speed (sec.) | | | | 17 | 11 | 9 |
| Exudation property (%) | | | | 28 | 26 | 24 |
| Back flow property (g) | | | | 1.9 | 1.3 | 1.3 |
| Random property (%) | | | | 55.4 | 54.8 | 56.7 |

TABLE 1-2

| | | | | Example | | | |
|---|---|---|---|---|---|---|---|
| | | | | 4 | 5 | 6 | 7 |
| Surface material | Long fiber layer | Long fiber | Type of fiber | Hot-melt-adhesive composite type | Hot-melt-adhesive composite type | Hot-melt-adhesive composite type | Hot-melt-adhesive composite type |
| | | | Used resin | PP/HDPE | PP/HDPE | PP/HDPE | PP/HDPE |
| | | | Denier | 2 d | 2 d | 2 d | 2 d |

TABLE 1-2-continued

| | | | Example | | | |
|---|---|---|---|---|---|---|
| | | | 4 | 5 | 6 | 7 |
| Short fiber layer | Metsuke (g/m$^2$) | | 14 | 14 | 14 | 14 |
| | Long fiber fleece-fixing method | | — | — | — | — |
| | Hot-melt-adhesive composite short fiber | Used resin | PP/HDPE | PP/HDPE | PP/HDPE | PP/HDPE |
| | | Crimp | Spiral type | Spiral type | Spiral type | Spiral type |
| | | Denier × cut length | $2^3 \times 30$** | $2^{\,3} \times 51$** | $2^d \times 5$** | $2^d \times 5$** |
| | Hydrophilic short fiber | Mixing ratio (wt. %) | 0 | 0 | 30 | 70 |
| | | Material | — | — | Rayon | Rayon |
| | | Denier × cut length | — | — | $3^d \times 5$** | $3^d \times 6$** |
| | Web-forming process | | Air-laid process | Air-laid process | Air-laid process | Air-laid process |
| | Metsuke (g/m$^2$) | | 12 | 12 | 12 | 12 |
| | Short fiber web-fixing | | — | — | — | — |
| | Combining method | | Hot air-heating process | Hot air-heating process | Hot air-heating process | Hot air-heating process |
| Composite non-woven | Shear strength | | ◯ | ◯ | ◯ | ◯ |
| | Surface feeling | | 10 | 10 | 10 | 8 |
| | Apparent density (g/cm$^3$) | | 0.029 | 0.025 | 0.032 | 0.040 |
| Permeation speed (sec.) | | | 8 | 8 | 8 | 8 |
| Exudation property (%) | | | 20 | 20 | 23 | 36 |
| Back flow property (g) | | | 1.2 | 1.3 | 1.3 | 1.8 |
| Random property (%) | | | 52.4 | 51.7 | 56.7 | 52.5 |

TABLE 2-1

| Body fluid-diffusing layer | | | | Example | | | |
|---|---|---|---|---|---|---|---|
| | | | | 8 | 9 | 10 | 11 |
| | Constituting fiber | Type of fiber | | Single type | Hot-melt-adhesive composite type | Hot-melt-adhesive composite type | Single type |
| | | Material | | PP | PP/LLDPE | PP/HDPE | PP |
| | | Denier × cut length | | $2^d \times 45^{}$ | $2^d \times 64^{}$ | $2^d \times 64^{}$ | $3^d \times 76^{}$ |
| | | Crimp | | Zigzag type | Spiral type | Spiral type | Zigzag type |
| | | Extent of added shape | | — | — | — | 1.3 |
| | | Hydrophilic component | Hydrophilyzing agent | Surfactant | Surfactant | Surfactant | Hydrophilic fiber |
| | | | Addition method | Incorporated | Surface-adhered | Surface-adhered | Incorporated |
| | | | Addition (wt. %) | 6.0 | 0.3 | 0.8 | 20 |
| | Mixed shore fibers or filaments | Mixing ratio (wt. %) | | 0 | 0 | 30 | 40 |
| | | Type of fiber | | — | — | Single type | Single type |
| | | Material | | — | — | Rayon | PET |
| | | Fiber length (mm) | | — | — | $4^d \times 51^{}$ | $10^d \times 89^{}$ |
| | | Crimp | | — | — | Zigzag type | Zigzag type |
| | | Extent of non-circular shape | | — | — | — | 2.2 |
| | | Hydrophilic component | Hydrophilyzing agent | — | — | Surfactant | Surfactant |
| | | | Addition method | — | — | Surface-adhered | Surface-adhered |
| | | | Addition (wt. %) | — | — | 0.3 | 0.4 |
| | Non-woven fabric making method | | | High pressure water stream process | Hot air heating process | Hot air heating process | Not carried out |
| | Metsuke (g/m²) | | | 48 | 62 | 70 | 146 |
| Permeation speed (sec.) | | | | 7 | 5 | 4 | 4 |
| Exudation property (%) | | | | 23 | 21 | 18 | 15 |
| Back flow property (g) | | | | 1.2 | 1.3 | 0.8 | 0.9 |
| Random property (%) | | | | 55.8 | 56.9 | 57.1 | 56.2 |

TABLE 2-2

| | | | Example | | | |
|---|---|---|---|---|---|---|
| | | | 12 | 13 | 14 | 15 |
| Body fluid-diffusing layer | Constituting fiber | Type of fiber | Hot-melt-adhesive composite type | Hot-melt-adhesive composite type | Single type composite type | Single type |
| | | Material | PP/HDPE | PP/HDPE | PP | PP |
| | | Denier × cut length | $3^d \times 64^{}$ | $3^d \times 51^{}$ | Long fiber $2^d$ | $0.35^d$ |
| | | Crimp | U-letter type | U-letter type | none | none |
| | | Extent of added shape | — | — | — | — |
| | | Hydrophilic component Hydrophilyzing agent Addition method Addition (wt. %) | Hydrophilic fiber Incorporated 0.3 | Surfactant Incorporated 0.2 | Surfactant Surface-adhered 0.3 | Surfactant Incorporated 9.8 |
| | Mixed shore fibers or filaments | Mixing ratio (wt. %) | 60 | 43 | 28 | 0 |
| | | Type of fiber | Hydrophilic fiber | Single type | Single type | — |
| | | Material | PET | PET | PP | — |
| | | Fiber length (mm) | $10^d \times 89^{}$ | $6^d \times 89^{}$ | Long fiber $2^d$ | — |
| | | Crimp | Zigzag type | Zigzag type | Spiral type | — |
| | | Extent of non-circular shape | 2.2 | 2.3 | — | — |
| | | Hydrophilic component Hydrophilyzing agent Addition method Addition (wt. %) | Surfactant Surface-adhered 0.3 | Surfactant Incorporated 0.5 | Surfactant Surface-adhered 0.3 | — |
| | Non-woven fabric making method | | Hot air heating process | Needle panching process | Not carried out | Emboss roll process |
| | Metsuke (g/m²) | | 35 | 72 | 95 | 85 |
| Permeation speed (sec.) | | | 4 | 4 | 4 | 7 |
| Exudation property (%) | | | 14 | 14 | 14 | 19 |
| Back flow property (g) | | | 0.9 | 0.8 | 0.9 | 1.3 |
| Random property (%) | | | 54.3 | 58.9 | 57.4 | 55.5 |

TABLE 3-1

|  |  |  | Comparative example | | |
|---|---|---|---|---|---|
|  |  |  | 1 | 2 | 3 |
| Long fiber layer | Long fiber | Type of fiber | Non-composite type | Non-composite type | Non-composite type |
|  |  | Used resin | PP | PP | PP |
|  |  | Denier | 2 d | 2 d | 2 d |
|  | Metsuke (g/m$^2$) |  | 14 | 14 | 14 |
|  | Long fiber fleece-fixing method |  | Emboss roll process | Emboss roll process | Emboss roll process |
| Short fiber layer | Hot-melt-adhesive composite short fiber | Used resin | PP/PE | PP/PE | PP/PE |
|  |  | Crimp | Zigzag type | Zigzag type | Zigzag type |
|  |  | Denier × cut length | 2$^d$ × 64** | 2$^d$ × 64** | 2$^d$ × 64** |
|  | Hydrophilic short fiber | Mixing ratio (wt. %) | 0 | 0 | 0 |
|  |  | Material | — | — | — |
|  |  | Denier × cut length | — | — | — |
|  | Web-forming process |  | Carding process (parallel) | Carding process (parallel) | Carding process (random) |
|  | Metsuke (g/m$^2$) |  | 12 | 12 | 12 |
|  | Short fiber web-fixing |  | Hot air-heating process | — | — |
| Combining method |  |  | Hot air-heating process | Hot air-heating process | Hot air-heating process |
| Shear strength |  |  | X | X | X |
| Surface feeling |  |  | 4 | 6 | 6 |
| Apparent density (g/cm$^3$) |  |  | 0.052 | 0.048 | 0.047 |
| Permeation speed (sec.) |  |  | 25 | 21 | 19 |
| Exudation property (%) |  |  | 108 | 85 | 66 |
| Back flow property (g) |  |  | 2.9 | 2.4 | 2.0 |
| Random property (%) |  |  | 30.6 | 31.6 | 37.6 |

TABLE 3-2

|  |  |  | Comparative example | | |
|---|---|---|---|---|---|
|  |  |  | 4 | 5 | 6 |
| Long fiber layer | Long fiber | Type of fiber | Non-composite type | Hot-melt-adhesive composite type | Hot-melt-adhesive composite type |
|  |  | Used resin | PP | PP/HDPE | PP/HDPE |
|  |  | Denier | 2 d | 2 d | 2 d |
|  | Metsuke (g/m$^2$) |  | 14 | 14 | 14 |
|  | Long fiber fleece-fixing method |  | Emboss roll process | — | — |
| Short fiber layer | Hot-melt-adhesive composite short fiber | Used resin | PP/PE | PP/PE | PP/PE |
|  |  | Crimp | Zigzag type | Spiral type | Spiral type |
|  |  | Denier × cut length | 2$^d$ × 64** | 2$^d$ × 64** | 2$^d$ × 64** |
|  | Hydrophilic short fiber | Mixing ratio (wt. %) | 0 | — | — |
|  |  | Material | — | — | — |
|  |  | Denier × cut length | — | — | — |
|  | Web-forming process |  | Random webber process | Carding process (parallel) | Air-laid process |
|  | Metsuke (g/m$^2$) |  | 12 | 12 | 12 |
|  | Short fiber web-fixing |  | — | — | — |
| Combining method |  |  | Hot air-heating process | Hot air-heating process | Hot air-heating process |
| Shear strength |  |  | X | Δ | Not measured due to inferior formation of composite non-woven fabric |
| Surface feeling |  |  | 6 | 6 |  |
| Apparent density (g/cm$^3$) |  |  | 0.044 | 0.44 |  |
| Permeation speed (sec.) |  |  | 19 | 20 |  |
| Exudation property (%) |  |  | 59 | 84 |  |
| Back flow property (g) |  |  | 1.8 | 2.4 |  |
| Random property (%) |  |  | 41.1 | 33.4 |  |

As apparent from Tables 1, 2 and 3, despite the fact that the top sheets of the absorptive articles of Examples are composed of a non-woven fabric of the same metsuke (Japanese term: weight of unit product) as that of Comparative Examples, the absorptive articles of Examples were superior in the surface hand feeling and further in all of shear stress, permeation speed, exudation property, back flow property, and random property. Since the absorptive articles of Examples have a low apparent density of the top sheet 2, they are superior in the surface hand feeling, low in the capillary-like function in the lengthwise direction of composite non-woven fabric, i.e. in the mechanical direction thereof and superior in the capillary-like function in the thickness direction of the combined non-woven fabric;

hence they are superior in the permeation speed, exudation property and low back flow property. Namely, the absorptive article of the present invention imparts a high random property upon the combined non-woven fabric used for at least the top sheet or the second sheet among the surface materials, whereby the absorptive articles of the present invention satisfy such characteristics as good permeation-absorption and spot-absorption of body fluids such as urine, sweat, and blood, dryish feeling, and low back-flow property of permeated body fluids all of which are intrinsic requirements of the absorptive articles such as disposable diapers, and sanitary napkins.

The absorptive articles of the invention have the following advantageous effects based upon the functions due to the above-mentioned structure:

(1) Since the capillary-like function in the lengthwise direction, i.e. mechanical direction of the combined non-woven fabric used as a surface material of the absorptive articles is difficult to occur, the articles have a superior spot absorptivity.

(2) Since the capillary-like function in the lengthwise direction, i.e. mechanical direction of the combined non-woven fabric used as a surface material of the absorptive articles is low, and the capillary-like function in the thickness direction of the composite non-woven fabric is superior, the absorptive articles are superior in the permeation-absorption of body fluids.

(3) Since the apparent density of the combined non-woven fabric used as the surface material is sufficiently low and the capillary-like function in the thickness direction of the non-woven fabric is superior, the flow back property of the permeated body fluids is low.

(4) Since the capillary-like function in the lengthwise direction, i.e. mechanical direction of the composite non-woven fabric used as the surface material is difficult to occur, the absorptive articles are superior in the dryish feeling.

(5) Since an anchor effect between the bonded layers of the long fiber non-woven fabric and the short fiber non-woven fabric is superior, the morphological (shape) stability against the dislocating stress and the twisting stress is superior.

(6) Since the apparent density of the combined non-woven fabric used as the surface material is sufficiently low, the bulkiness and the surface hand feeling of the absorptive articles are good and the their skin feeling is superior.

(7) Since the random property of the fibers in the short fiber non-woven fabric which constitute the combined non-woven fabric used as the surface material is high, and the short fibers which constitute the short fiber non-woven fabric are mainly arranged in the thickness direction of the non-woven fabric, cushion property of The absorptive articles is superior.

Description in the present specification has been made mainly with reference to the case where the absorptive articles are sanitary napkin but the absorptive articles of the present invention can preferably be used even for disposable diapers, pads for incontinence, and sheets for discharge from the womb, and the like.

What is claimed is:

1. An absorptive article containing a surface material comprising a combined non-woven fabric comprising at least two layers of a long fiber non-woven fabric and a short fiber non-woven fabric joined together, and an absorbing body for retaining a body fluid, said short fiber non-woven fabric being composed of hot-melt-adhesive composite short fibers having at least two kinds of thermoplastic resin components of a high melting point component and a low melting point component, said hot-melt-adhesive composite short fibers being hot-melt-adhered together, the crossing angle of said short fibers at at least 45% of the total contact points in said short fiber non-woven fabric being occupied by an angle of 60° to 90° in the analysis of the distribution of the crossing angle at the contact points of said short fibers wherein said crossing angle of 60° to 90° at at least 45% of the total contact points in said short fiber non-woven fabric is determined by measuring the smallest angle among four angles formed at the contact point of short fibers which are crossed.

2. The absorptive article according to claim 1 wherein a body fluid-diffusing layer is interposed between said surface material and said absorbing body.

3. The absorptive article according claim 2, wherein said body fluid-diffusing layer is an aggregate of crimped fibers.

4. The absorptive article according to claim 3 wherein said body fluid-diffusing layer is an aggregate of fibers comprising mixed long fibers or mixed short fibers.

5. The absorptive article according to claim 2 wherein said body fluid-diffusing layer is an aggregate of fibers comprising mixed long fibers or mixed short fibers.

6. The absorptive article according to claim 5 wherein said body fluid-diffusing layer is an aggregate of fibers having an not-circular cross-section.

7. The absorptive article according to claim 2 wherein said body fluid-diffusing layer is an aggregate of fibers having an not-circular cross-section.

8. The absorptive article according to claim 7 wherein said body fluid diffusing layer is an aggregate of fibers containing a hydrophilic component.

9. The absorptive article according to claim 2 wherein said body fluid diffusing layer is an aggregate of fibers containing a hydrophilic component.

10. The absorptive article according to claim 1 wherein said long fiber non-woven fabric is composed of hot-melt-adhesive composite long fibers having at least two kinds of thermoplastic resin components of a high melting point component and a low melting point component, and the contact points between the hot-melt-adhesive composite long fibers are hot-melt-adhered.

11. The absorptive article according to claim 1, wherein said short fiber non-woven fabric is composed of fibers having a fiber length of 3 to 51 mm.

12. The absorptive article according to claim 11 wherein said short fiber non-woven fabric is composed of (A) hot-melt-adhesive composite short fibers having at least two kinds of thermoplastic resin components of a high melting point component and a low melting point component, and (B) hydrophilic short fibers, and the fiber mixing ratio of A/B is 30/70 to 100/0.

13. The absorptive article according to claim 11 wherein said short fiber non-woven fabric has a density gradient in the thickness direction of said non-woven fabric.

14. The absorptive article according to claim 1 wherein said short fiber non-woven fabric is composed of (A) hot-melt-adhesive composite short fibers having at least two kinds of thermoplastic resin components of a high melting point component and a low melting point component, and (B) hydrophilic short fibers, and the fiber mixing ratio of A/B is 30/70 to 100/0.

15. The absorptive article according to claim 14 wherein said short fiber non-woven fabric has a density gradient in the thickness direction of said non-woven fabric.

16. The absorptive article according to claim 1, wherein said short fiber non-woven fabric has a density gradient in the thickness direction of said non-woven fabric.

* * * * *